United States Patent
Vinciguerra et al.

(10) Patent No.: US 11,696,708 B2
(45) Date of Patent: Jul. 11, 2023

(54) PROBE DEVICE AND SPECTROSCOPY SYSTEM INCLUDING A STRUCTURE WITH A PLURALITY OF HOUSINGS FOR LIGHTING AND DETECTION DEVICES

(71) Applicant: STMicroelectronics S.r.l., Agrate Brianza (IT)

(72) Inventors: Vincenzo Vinciguerra, Biancavilla (IT); Piero Fallica, Catania (IT); Mario Francesco Romeo, Fiumefreddo di Sicilia (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 574 days.

(21) Appl. No.: 16/824,374

(22) Filed: Mar. 19, 2020

(65) Prior Publication Data
US 2020/0305778 A1 Oct. 1, 2020

(30) Foreign Application Priority Data
Mar. 25, 2019 (IT) .......................... 102019000004311

(51) Int. Cl.
| | | |
|---|---|---|
| A61B 5/1455 | (2006.01) | |
| A61B 5/25 | (2021.01) | |
| A61B 5/0245 | (2006.01) | |
| A61B 5/00 | (2006.01) | |
| A61B 5/291 | (2021.01) | |
| A61B 5/026 | (2006.01) | |
| A61B 5/268 | (2021.01) | |

(52) U.S. Cl.
CPC ........ *A61B 5/14552* (2013.01); *A61B 5/0245* (2013.01); *A61B 5/0261* (2013.01); *A61B 5/268* (2021.01); *A61B 5/291* (2021.01); *A61B 5/6803* (2013.01); *A61B 5/6848* (2013.01)

(58) Field of Classification Search
CPC ... A61B 5/4064; A61B 5/6848; A61B 5/0245; A61B 5/0291; A61B 5/6803; A61B 5/1455; A61B 5/14551; A61B 5/14552; A61B 5/0075; A61B 5/25; A61B 5/14553; A61B 5/0205; A61B 2562/046; A61B 2562/0209
See application file for complete search history.

(56) References Cited

U.S. PATENT DOCUMENTS

| | | |
|---|---|---|
| 2004/0082862 A1 | 4/2004 | Chance |
| 2010/0056880 A1* | 3/2010 | Cho ................... A61B 5/02438 600/509 |

(Continued)

FOREIGN PATENT DOCUMENTS

| | | |
|---|---|---|
| JP | 2006-223503 A | 8/2006 |
| WO | 2018/199977 A1 | 11/2018 |

OTHER PUBLICATIONS

Ameri et al., "Graphene Electronic Tattoo Sensors," *ACS Nano* 11, 2017, pp. 7634-7641.

(Continued)

*Primary Examiner* — Chu Chuan Liu
(74) *Attorney, Agent, or Firm* — Seed IP Law Group LLP

(57) ABSTRACT

A probe device includes an optical device including at least one of a photodetector or a first light source. A cover structure is included and is arranged in front of the optical device. The cover structure includes an electrode which contacts, in use, a body tissue.

20 Claims, 12 Drawing Sheets

(56) References Cited

U.S. PATENT DOCUMENTS

| | | | | |
|---|---|---|---|---|
| 2012/0071734 A1* | 3/2012 | Shimuta | ............... | A61B 5/332 |
| | | | | 600/301 |
| 2012/0310071 A1* | 12/2012 | Nakao | ................ | A61B 5/0537 |
| | | | | 600/393 |
| 2013/0328051 A1* | 12/2013 | Franklin | .............. | G06F 1/1637 |
| | | | | 361/679.01 |
| 2014/0151586 A1* | 6/2014 | Shimuta | ................. | A61B 5/25 |
| | | | | 250/578.1 |
| 2015/0238100 A1 | 8/2015 | Lin et al. | | |
| 2017/0311898 A1 | 11/2017 | Bae et al. | | |

OTHER PUBLICATIONS

Beach et al., "Wearable Heart Rate Monitoring with Inkjet-Printed Graphene," The University of Manchester Research, 2018, 2 pages.

Celik, "Wireless Graphene-Based Electrocardiogram (ECG) Sensor Including Multiple Physiological Measurement System," Thesis, Brunel University London, Aug. 7, 2017, 196 pages.

Liu et al., "Flexible, Stretchable Sensors for Wearable Health Monitoring: Sensing Mechanisms, Materials, Fabrication Strategies and Features," *Sensors 18*, 2018, 35 pages.

Lou et al., "Flexible Graphene Electrodes for Prolonged Dynamic ECG Monitoring," *Sensors 16*, 2016, 12 pages.

Scherzinger et al., "Development of Graphene-Based Ionizing Radiation Sensors," Poster, retrieved from https://agenda.infn.it/getFile.py/access?contribId=271&sessionId=13&resId=0&materialId=13450, 1 page.

Sultana et al., "CMOS silicon avalanche photodiodes for NIR light detection: a survey," *Analog Integr Circ Sig Process 70*, 2012, 13 pages.

* cited by examiner

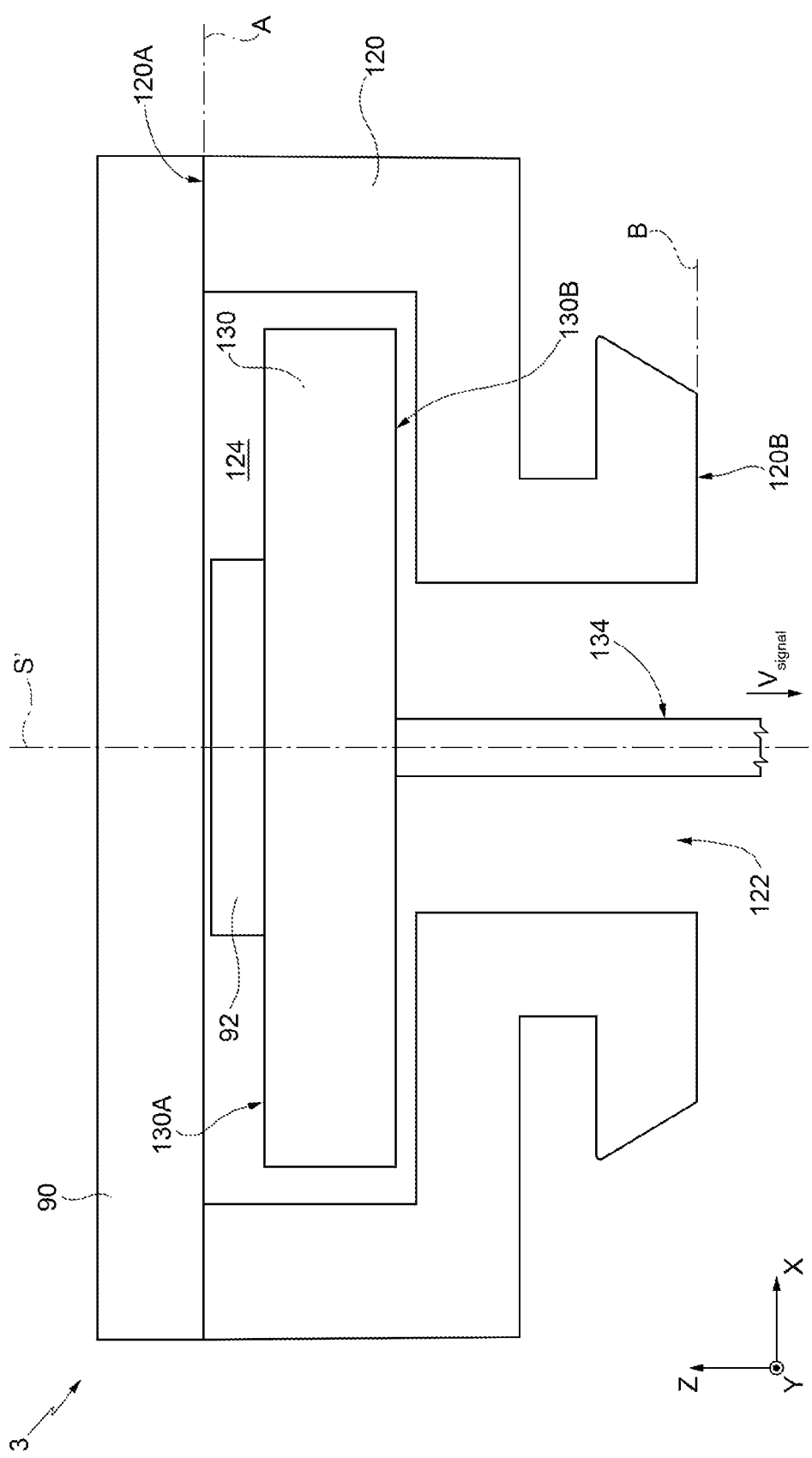

PROBE DEVICE AND SPECTROSCOPY SYSTEM INCLUDING A STRUCTURE WITH A PLURALITY OF HOUSINGS FOR LIGHTING AND DETECTION DEVICES

BACKGROUND

Technical Field

The present disclosure relates to a probe device and functional spectroscopy system, which includes a structure that may be coupled to a body tissue and comprises a plurality of housings designed to house lighting and detection devices.

Description of the Related Art

As is known, functional spectroscopy, and in particular functional near-infrared spectroscopy (fNIRS), is a non-invasive technique of analysis of body tissues; for example, this technique is used for analysis of the brain tissue and, in particular, for brain-activity imaging.

In detail, a generic system using the fNIRS technique (referred to hereinafter also as a fNIRS system) uses light sources (for example, laser sources or LEDs) that emit radiation in the near infrared (i.e., with wavelengths comprised between 650 nm and 950 nm), since, for this radiation, the absorption of the light radiation by the body tissue is low. Further, notwithstanding the presence of a significant scattering, the light radiation that impinges upon the body tissue is in any case able to diffuse for several centimeters within the tissue before being absorbed or reflected by the latter.

The light radiation reflected by the body tissue is then detected by at least one detector, which also forms part of the fNIRS system. In particular, the detector generates and sends a signal (for example, a voltage signal), representing the radiation detected, to a processing system. The processing system is able to determine various parameters, starting from the signal generated by the detector.

For instance, since the light radiation is principally absorbed by the oxygenated hemoglobin ($HbO_2$) and by the deoxygenated hemoglobin (HHb), which are both present in the blood flow, the processing system is able to determine, by the known Lambert-Beer law, the volume of blood, the variation in time of concentration, and the degree of oxygenation of the hemoglobin in the blood of the tissue analyzed.

In greater detail, to estimate the variations in time of the hemoglobin concentration, each fNIRS system may use at least two light sources, which emit, respectively, a light radiation with a wavelength shorter than 800 nm (for example, 735 nm) and another light radiation with a wavelength longer than 800 nm (for example, 850 nm). In use, the two light sources are activated in a sequential way, i.e., in an alternating way, so as to prevent possible errors due to the optical interference between the light sources themselves.

Irrespective of the number of light sources, known fNIRS systems may implement different types of data-acquisition techniques, such as:

the time-resolved (TR) spectroscopy method, where the time of flight of the photons generated by a pulsed source (which, for example, emits pulses with a duration of the order of nanoseconds) within the body tissue is recorded; this method enables determination of information on the absorption and scattering of the photons in the tissue under examination;

the continuous-wave (CW) spectroscopy method, where sources are used that emit light radiation for relatively long periods of time (for example, with a duration comprised between 1 s and 10 ms) and where variations in the intensity of the light detected are used to determine the variations in the absorption of the light radiation emitted by the sources; and the frequency-domain spectroscopy method, where the light sources emit radiofrequency-modulated light radiation, and where the amplitude and phase of the reflected radiation are measured.

Considering, for example, just the fNIRS systems that enable continuous-wave functional near-infrared spectroscopy (CW-fNIRS) to be carried out, also referred to as CW-fNIRS systems, solutions are known based upon two different detection and data-acquisition approaches, for example for recording brain activity.

According to a first approach, the CW-fNIRS system includes a first plurality and a second plurality of optical fibers, which are configured, respectively, to guide the light radiation emitted by one or more light sources as far as the scalp of a patient, as well as to collect the light radiation reflected by the scalp of the patient being examined. In this case, the optical fibers are typically multimode optical fibers.

The first approach is typically used when the entire cerebral cortex is to be analyzed, in order to obtain a complete analysis of the brain activity.

According to a second approach, the CW-fNIRS system uses pairs formed by a light source and by a corresponding detector (which are arranged at a distance from one another, for example, comprised between 1 cm and 3 cm), which are fixed on a corresponding flexible support, which is directly positioned on the scalp of the patient. In particular, these supports are of small dimensions (for example, a support that carries just one pair may have dimensions of 4 cm×4 cm) and the distance between each light source and the corresponding detector is such as to maintain optical coupling between them.

Thanks to the above characteristics, the second approach is used when only some portions of brain tissue are to be analyzed since the flexible supports may be easily positioned in the regions of interest.

Unfortunately, the known solutions discussed in the foregoing paragraphs present some disadvantages.

In particular, a CW-fNIRS system that uses the first approach typically presents high power losses, due to the optical couplings between the light sources and the optical fibers, in addition to the optical couplings between the optical fibers and the detectors. These losses in turn cause a considerable reduction in the sensitivity of the CW-fNIRS system. Further, since the CW-fNIRS system uses a certain number of optical fibers, the process of analysis is troublesome for the patient, in so far as the ensemble of the optical fibers is cumbersome and heavy.

In the case of a CW-fNIRS system that uses the second approach, instead, the arrangement of the light source and of the detector of each pair is substantially fixed. Further, it is not possible to conduct easily an analysis of the entire scalp of the patient, given the small dimensions of the supports. In fact, in the case where it is desired to analyze a wide region of tissue, not only are a larger number of light sources and detectors used, but also such sources generally have relatively higher power consumption.

Basically, the above problems occur also in other kind of spectroscopy systems, such as photopletysmographic (PPG) systems.

In addition, in case a body tissue has to be subjected to either a spectroscopic analysis and an analysis of corresponding electrical signals, such as an electroencephalography (EEG) or an electrocardiography (ECG), different probes have to be used; that implies the adoption of a highly complex layout of probes.

BRIEF SUMMARY

In various embodiments, the present disclosure provides a probe device that will enable the drawbacks of the prior art to be overcome at least in part.

According to the present disclosure, a probe device and a spectroscopy system are provided.

In at least one embodiment, a probe device includes an optical device including at least one of a photodetector or a first light source. A cover structure is included and is arranged in front of the optical device and includes an electrode, the electrode being configured to contact, in use, a body tissue.

In at least one embodiment, a spectroscopy system is provided that includes a plurality of lighting devices. Each of the lighting devices includes a first light source and a first cover structure arranged in front of the first light source. The first cover structure includes a first electrode that is configured to contact a body tissue. A plurality of detection devices is further included, and each of the detection devices includes a photodetector and a second cover structure arranged in front of the photodetector. The second cover structure includes a second electrode that is configured to contact the body tissue. A wearable structure is included and is configured to be mechanically coupled to the body tissue. The wearable structure includes a plurality of housings, and each of the housings is configured to house a corresponding lighting device or a corresponding detection device.

In one or more embodiments, a device is provided that includes a housing which defines a first cavity and a second cavity. A substrate is disposed in the first cavity, and an optical structure is disposed on the substrate. The optical structure includes at least one of a photodetector or a light source. A dielectric cap is disposed on the first cavity, and the first cavity is disposed between the dielectric cap and the second cavity. An electrode is provided on the dielectric cap, and the electrode is configured to contact, in use, a body tissue.

BRIEF DESCRIPTION OF THE SEVERAL VIEWS OF THE DRAWINGS

For a better understanding of the present disclosure, a preferred embodiment thereof is now described, purely by way of non-limiting example, with reference to the attached drawings, wherein:

FIG. 4 is a schematic cross-sectional illustration of a detection device;

DETAILED DESCRIPTION

Figure 1:
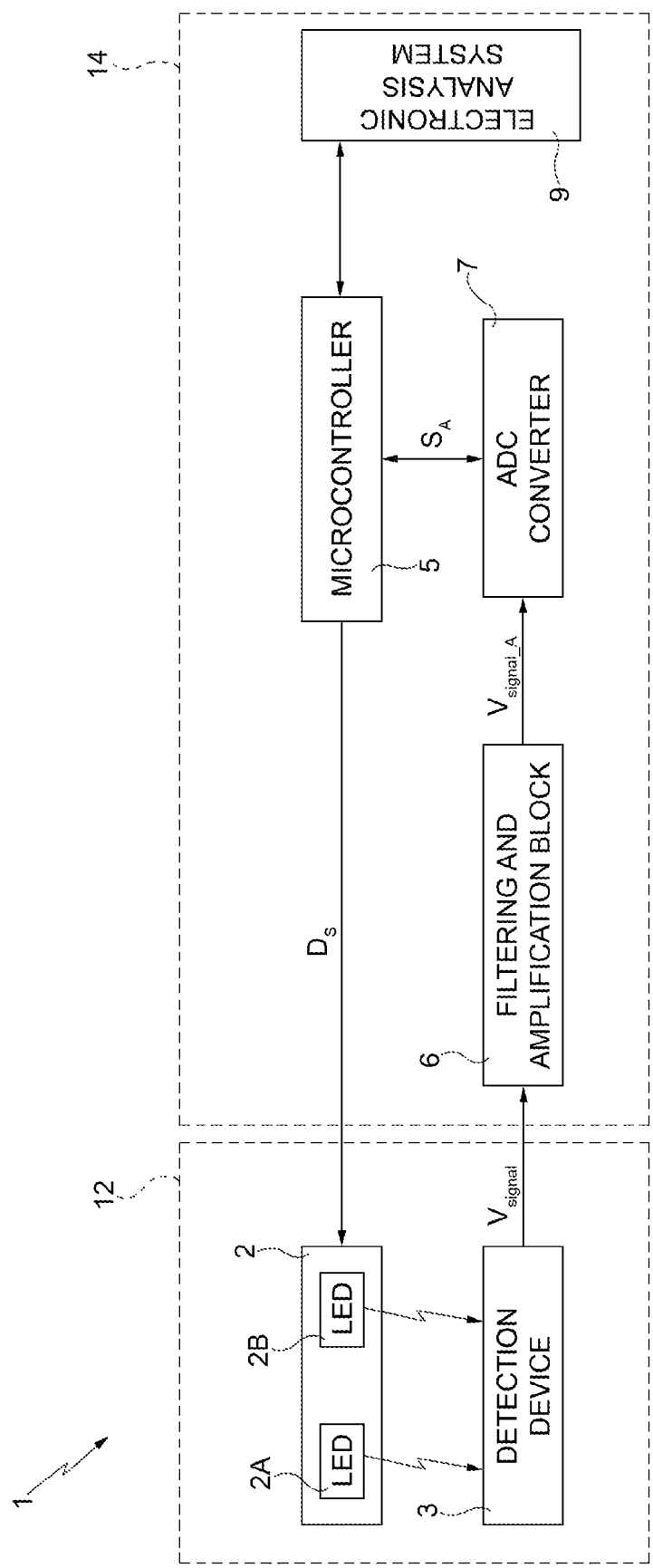
FIG. 1 shows a block diagram of the present functional spectroscopy system.

FIG. 1 shows a functional spectroscopy system 1 (hereinafter, also referred to as fNIRS system 1), which, without this implying any loss of generality, is assumed as implementing the continuous-wave detection method. Once again without this implying any loss of generality, it is assumed that the fNIRS system 1 is designed for analysis of brain activity.

In particular, the fNIRS system 1 comprises an optical detection system 12 and a processing and analysis system 14, electrically coupled to one another.

In detail, the optical detection system 12 comprises a plurality of lighting devices 2 (just one of which is illustrated in FIG. 1) that are the same as one another, and a plurality of detection devices 3 (just one of which is illustrated in FIG. 1) that are the same as one another.

In general, each lighting device 2 comprises a first light source 2A and a second light source 2B that may be formed by corresponding LEDs. In particular, the first and second light sources 2A, 2B emit light radiation in the near infrared at different wavelengths. For instance, the first light source 2A emits a first light radiation, having a wavelength shorter than 800 nm (for example, 735 nm), whereas the second light source 2B emits a second light radiation, having a wavelength longer than 800 nm (for example, 850 nm). In this way, the processing and analysis system 14 may determine, among the parameters for the body tissue being investigated, the variations in time of the concentrations of oxygenated hemoglobin and of deoxygenated hemoglobin in the blood.

Figure 2:
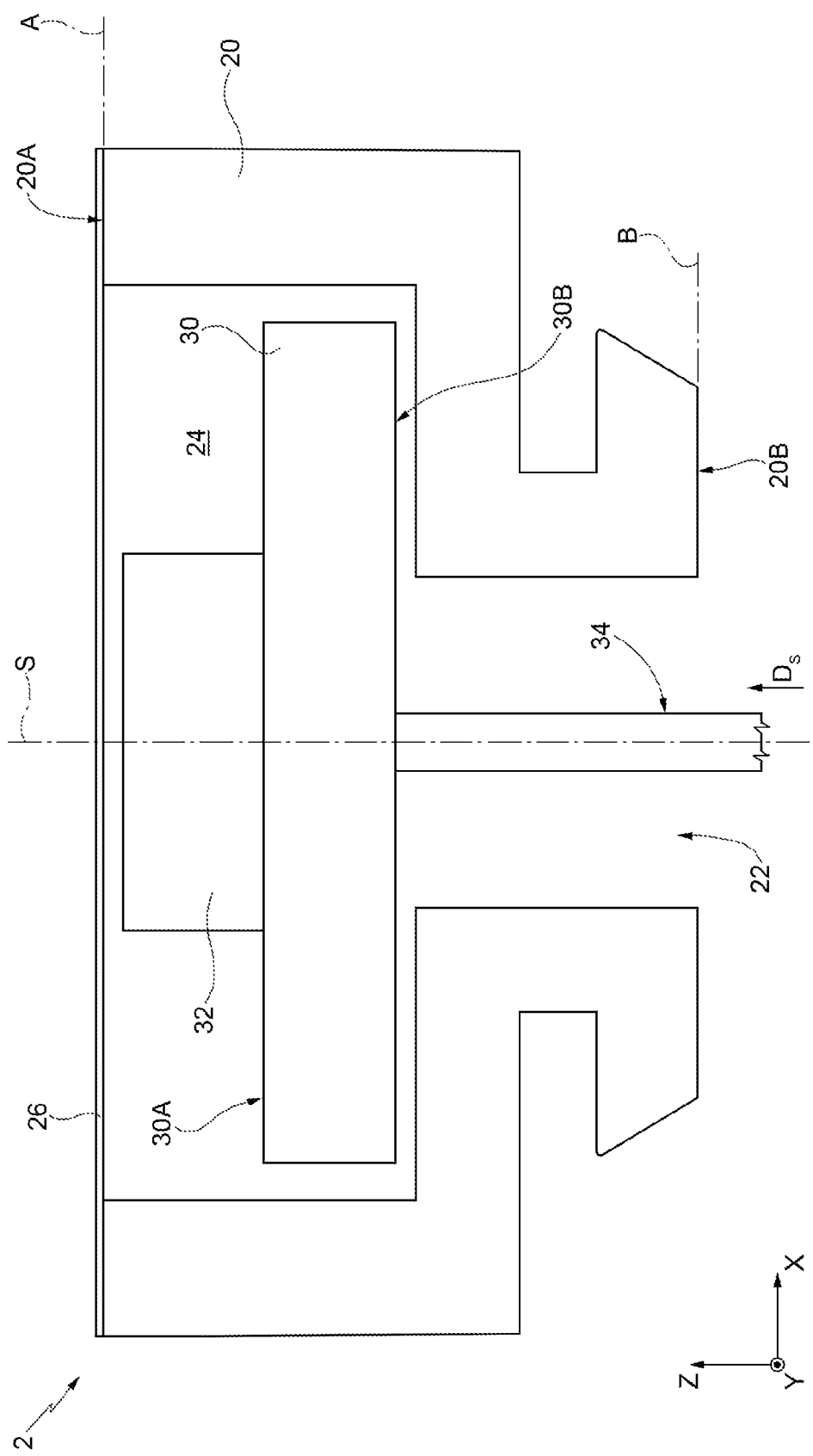
FIG. 2 is a schematic cross-sectional illustration of a lighting device.

FIG. 2 shows a possible example of one lighting device 2.

In detail, the lighting device 2 comprises a container 20, for example of PVC (polyvinyl chloride), which is delimited at the top and at the bottom, respectively, by a first surface 20A and a second surface 20B, which define, respectively, a first plane of extension A and a second plane of extension B (which are illustrated dashed in FIG. 2) both parallel to a plane XY of a Cartesian reference system XYZ.

Further, the container 20 has, for example, a hollow circular shape in top plan view, with axis of symmetry S parallel to a first axis Z of the reference system XYZ.

In greater detail, the container 20 delimits a main cavity 24 and a secondary cavity 22, which are in communication with one another. In particular, the main cavity 24 has a cylindrical shape, gives out onto the first surface 20A and overlies the secondary cavity 22, which also has a cylindrical shape, has a diameter smaller than the diameter of the main cavity 24, is aligned with the main cavity 24 along the axis of symmetry S, and gives out onto the bottom surface 20B.

Present inside the main cavity 24 is a substrate 30, which is delimited by a top surface 30A and a bottom surface 30B; in particular, the substrate 30 is made, for example, of FR4 and is of a flexible type. Further, the substrate 30 may have a cylindrical shape, with an axis coinciding with the axis of symmetry S and with a diameter comprised between the diameter of the main cavity 24 and the diameter of the secondary cavity 22. Albeit not illustrated, extending within the substrate 30 are electronic circuits and conductive paths.

Extending on the top surface 30A is a bicolor LED emitter 32, which is functionally equivalent to the first and second light sources 2A, 2B and is electrically coupled to the electronic circuits and to the conductive paths formed in the substrate 30, which are in turn electrically coupled to an electrical cable 34 that enables connection of the lighting device 2 to the processing and analysis system 14 for managing operation of the lighting device 2 in the various operating steps.

The lighting device 2 also comprises a cap 26, arranged on the first surface 20A of the container 20 so as to close the main cavity 24 at the top. The cap 26 is made of a dielectric material, such as, for example, polyimide (such as Kapton®) or polyethylene laminas (such as PEN/PET—polyethylene naphthalate/polyethylene terephthalate), so as to present a high transmittance in the near infrared (for example, higher than 90%); further, the cap 26 has a thickness (i.e., an extension along the first axis Z) of, for example, 0.2 mm.

Figure 3:
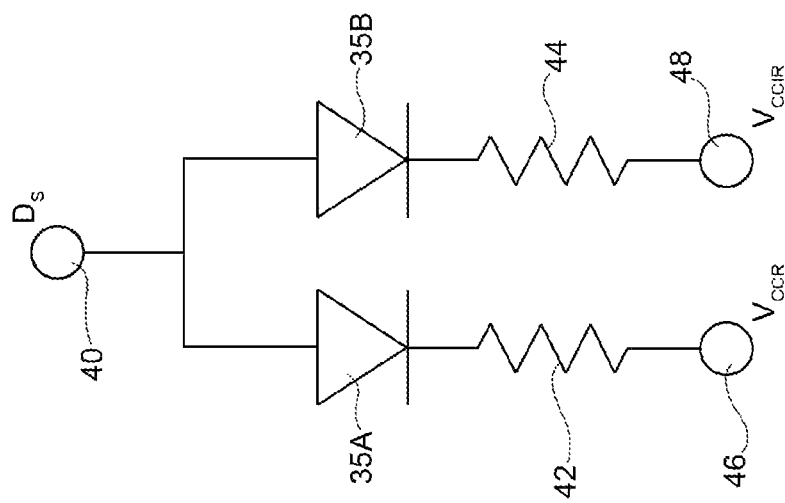
FIG. 3 shows an equivalent electrical diagram of a portion of the lighting device illustrated in FIG. 2.

As illustrated in FIG. 3, the bicolor LED emitter 32 is electrically equivalent to a first LED 35A and a second LED 35B, each having respective anode and cathode terminals. Further, FIG. 3 shows a first resistor 42 and a second resistor 44, each having a first terminal and a second terminal. The first and second resistors 42, 44 are designed, in use, to polarize, respectively, the first and second LEDs 35A, 35B, and both have a resistance comprised, for example, in the range between 10Ω and 1 kΩ.

In particular, the anode terminals of the first and second LEDs 35A, 35B are connected to a control terminal 40. On the other side, the cathode terminals of the first and second LEDs 35A, 35B are connected, respectively, to corresponding first terminals of the first and second resistors 42, 44. In addition, the second terminals of the first and second resistors 42, 44 are respectively connected to a first supply terminal 46 and to a second supply terminal 48, which are set in use, respectively, at a first supply voltage $V_{CCR}$ and a second supply voltage $V_{CCIR}$. The control terminal 40 and the first and second supply terminals 46, 48 are connected to the processing and analysis system 14 through the electrical cable 34.

In use, the processing and analysis system 14 controls the first and second supply voltages $V_{CCR}$, $V_{CCIR}$ and sends a driving signal Ds on the control terminal 40 so that the first and second LEDs 35A, 35B are turned on in an alternating way, emitting, respectively, the first light radiation and the second light radiation. In this connection, having assumed that the fNIRS system 1 is of the continuous-wave type, the first and second LEDs 35A, 35B are alternatively turned on for a relatively long period of time (for example, for periods comprised between 1 s and 10 ms).

FIG. 4 shows in detail a single detection device 3 of the fNIRS system 1, which is now described limitedly to the differences with respect to the lighting device 2. Components of the detection device 3 that are already present in the lighting device 2 are designated by the same references increased by 100, except where otherwise specified.

In detail, the detection device 3 comprises a photodetector 92, formed, for example, by a silicon photomultiplier (SiPM), which is formed by an array of Geiger-mode avalanche photodiodes (GAPDs), also known as single-photon avalanche diodes (SPADs).

The photodetector 92 is arranged on the top surface 130A of the substrate 130 and is electrically coupled to the electronic circuits and to the conductive paths of the substrate 130 (which are not illustrated), which are coupled to the processing and analysis system 14 through the electrical cable 134. In this way, the processing and analysis system 14 receives an output signal $V_{signal}$, generated by the photodetector 92 as a function of the light radiation reflected by the brain tissue, as described hereinafter.

The detection device 3 further comprises an optical filter 90, which is arranged on the first surface 120A of the container 120 so as to close the main cavity 124 and so as to overlay, at a distance, the photodetector 92.

In greater detail, the optical filter 90 is made, for example, of a dielectric material, such as plastic (for example, polyester or polycarbonate, or an organic glass, such as CR39); further, the optical filter 90 is a high-pass filter for the frequencies in the near infrared with a cut-on wavelength of, for example, 700 nm. In this way, the optical filter 90 is able to let through the environmental radiation having a wavelength equal to or longer than 700 nm, filtering out, instead, the background light, which could introduce errors due to phenomena of optical interference.

The containers of the lighting devices 2 and of the detection devices 3 may be the same as one another.

Figure 5:
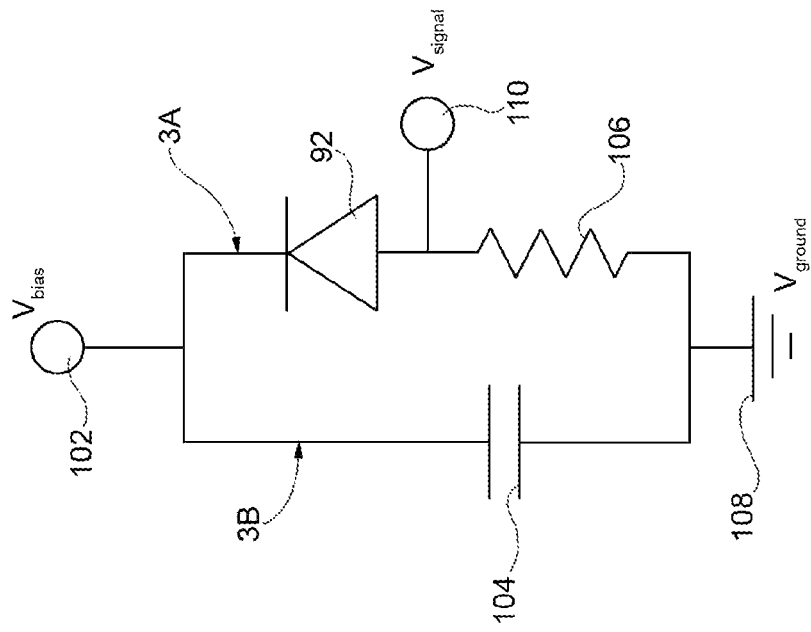
FIG. 5 shows an equivalent electrical diagram of a portion of the detection device illustrated in FIG. 4.

As illustrated in FIG. 5, the photodetector 92 is set in an electrical circuit comprising a first branch 3A and a second branch 3B, arranged in parallel with one another and arranged between a biasing terminal 102, which in use is set at a biasing voltage $V_{bias}$, and a reference terminal 108 set at a reference voltage $V_{ground}$.

The first branch 3A comprises the photodetector 92, the cathode terminal of which is connected to the biasing terminal 102, and an output resistor 106, having a first terminal and a second terminal, which are connected to the anode terminal of the photodetector 92 and to the reference terminal 108, respectively. The anode terminal of the photodetector 92 and the first terminal of the output resistor 106 form an output node 110. For instance, the output resistor 106 has a resistance of 1 kΩ. The biasing terminal 102, the reference terminal 108, and the output node 110 are electrically connected to the processing and analysis system 14, through the conductive paths that extend in the substrate 130 and through the electrical cable 134.

In use, the photodetector 92 is reversely biased by the biasing voltage $V_{bias}$, the latter being higher (in modulus) than the breakdown voltage of the photodetector 92.

The second branch 3B comprises a capacitor 104, having a first terminal and a second terminal, which are respectively connected to the biasing terminal 102 and to the reference-potential terminal 108; by way of example, the capacitor 104 has a capacitance of 100 nF. Further, the capacitor 104 acts, in use, as a voltage-filtering and voltage-stabilization element for the photodetector 92.

Operatively, the photodetector 92 receives the reflected (or backscattered) radiation (more precisely, fractions thereof) coming from the brain tissue, as the first radiation or the second radiation emitted by the bicolor LED emitter 32 impinges upon the brain tissue, generating a corresponding current, with consequent generation, on the output node 110, of the output signal $V_{signal}$, which is received by the processing and analysis system 14.

Once again with reference to FIG. 1, the processing and analysis system 14 is described now in greater detail, with reference to the interaction with a single lighting device 2 and a single detection device 3, except where otherwise specified. In other words, reference is made the corresponding analysis of a portion of the brain tissue, optically coupled to the lighting device 2 and to the detection device 3 considered.

This having been said, the processing and analysis system 14 comprises: a microcontroller 5, electrically coupled to the lighting device 2 by the electrical cable 34; a filtering and amplification block 6, coupled to the detection device 3 by the electrical cable 134; an ADC (analog-to-digital converter) 7, electrically coupled to the filtering and amplification block 6 and to the microcontroller 5; and an electronic analysis system 9, coupled to the microcontroller 5.

In use, the microcontroller 5 controls the bicolor LED emitter 32 so as to turn on the first and second LEDs 35A, 35B in an alternating way. For example, the microcontroller 5 controls the first and second LEDs 35A, 35B so that each has an ON time comprised in the range of, for example, 1 µs to 10 ms.

Considering either the first light radiation or the second light radiation, this impinges upon the brain tissue and propagates in the latter. Part of the light radiation is absorbed by the brain tissue, whereas the remaining portion is reflected after propagating for some centimeters within the brain tissue; a corresponding reflected radiation is thus generated. In particular, according to whether the first or second light radiation impinges upon the brain tissue, a first reflected radiation or a second reflected radiation, respectively, is generated, the first reflected radiation and the second reflected radiation being received, in an alternating way, by the photodetector 92.

In particular, considering either the first reflected light radiation or the second reflected light radiation, this impinges upon the detection device 3, which generates the aforementioned output signal $V_{signal}$. For instance, the detection device 3 may operate in a free-running condition, i.e., so that detection of the reflected light radiation is made in a continuous way. Once again with reference to the output signal $V_{signal}$, since the first light radiation and the second light radiation, and thus also the first reflected light radiation and the second reflected light radiation, are generated in an alternating way, said output signal represents, alternatively, the first reflected radiation or the second reflected radiation.

Next, the output signal $V_{signal}$ is sent to the filtering and amplification block 6, which reduces the noise due to the electronic components and amplifies the output signal $V_{signal}$. Consequently, at output from the filtering and amplification block 6, an amplified output signal $V_{signal\_A}$ is present.

The amplified output signal $V_{signal\_A}$ is transmitted to the ADC 7, which converts the amplified output signal $V_{signal\_A}$ into a digital signal, referred to hereinafter as the analysis signal $S_A$.

The analysis signal $S_A$ is subsequently sent to the microcontroller 5, which in turn sends it to the electronic analysis system 9 by known interfacing systems. Then, the analysis signal $S_A$ is processed by the electronic analysis system 9 so as to determine parameters regarding the brain activity. For instance, if the analysis signal generated in response to the first reflected radiation and the second reflected radiation are referred to as first and second analysis signals $S_{A1}$, $S_{A2}$, the processing system 9 may process in a per se known manner the first and second analysis signals $S_{A1}$, $S_{A2}$ to determine the concentrations of the oxygenated hemoglobin and of the deoxygenated hemoglobin.

Figure 6:
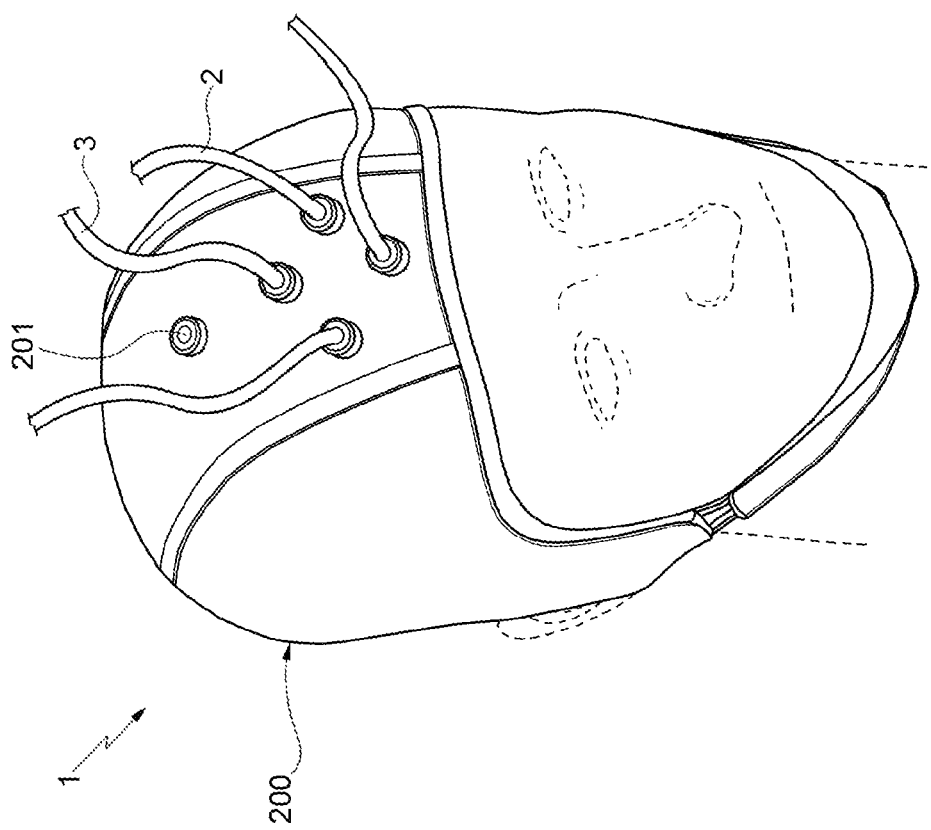
FIG. 6 shows a perspective view of a wearable structure.

As illustrated in FIG. 6, the fNIRS system 1 further includes a wearable structure 200 in the form of a helmet or headset, which is arranged on the scalp of the patient under examination.

The wearable structure 200 comprises a plurality of housings 201, each of which is designed to house indifferently a lighting device 2 or else a detection device 3. In other words, considering any housing 201, an operator may insert therein either a lighting device 2 or else a detection device 3 indifferently. Further, if by "probe device" is meant one of the lighting devices 2 or one of the detection devices 3, considering any housing 201, the mechanical coupling between the probe device and the housing is, for example, of the press-fit type, or else of an elastic type, and enables fixing of the probe device in the housing 201 in a releasable way. The probe device is thus arranged in contact with the scalp of the patient, to which it is temporarily fixed. In particular, in the case of a lighting device 2, the corresponding cap 26 contacts the scalp. Instead, in the case of a detection device 3, the scalp contacts the corresponding optical filter 90.

Without this implying any loss of generality, the housings 201 are arranged according to a mesh-like arrangement; i.e., they are arranged at the nodes of a hypothetical mesh, which covers the entire wearable structure 200.

For practical purposes, an operator may choose whether to connect the lighting devices 2 and the detection devices 3 in corresponding housings 201 so as to cover the entire scalp (i.e., by coupling all the housings 201 to corresponding probe devices), or else just a portion of scalp, so as to focus analysis on this portion. In addition, an operator may arrange the lighting devices 2 and the detection devices 3 in the corresponding housings 201 so that each lighting device 2 is operatively coupled to at least one corresponding detection device 3, i.e., so that the detection device 3 is able to receive, following upon reflection by the brain tissue, at least part of the first light radiation and of the second light radiation emitted by the lighting device 2. In other words, it is for example possible for each detection device 3 to be arranged in a corresponding housing 201 that is adjacent to a corresponding housing 201 that houses a lighting device 2, where by "adjacent" is meant that it is arranged at a distance such as to enable optical coupling between the detection device 3 and the lighting device 2.

The advantages that the present fNIRS system affords emerge clearly from the foregoing description.

In particular, the present fNIRS system enables a considerable reduction of the losses due to the optical coupling in so far as both the light sources and the photodetectors are arranged on the scalp of the patient being examined, without any need to resort to guiding structures, such as optical fibers. Further, the fNIRS system provides a high degree of flexibility for the operator, who may vary the relative arrangements, and thus also the distances, between the lighting devices and the detection devices.

Further, any interference due to the external environment is attenuated, since the present fNIRS system comprises a plurality of filters that are able to reduce considerably the disturbance deriving from the external environment.

In addition, the present fNIRS system is able to analyze the brain tissue to a greater depth in so far as not only is there a better optical coupling between light sources and photodetectors, but each photodetector (in particular, in the case of the silicon photomultiplier) has a high sensitivity. This advantage thus enables use of light sources that consume little power, such as low-power LEDs, without any significant losses in terms of quality of the analysis signals $S_A$.

In addition, both the light sources and the photodetectors are electrically insulated from the body tissue, with consequent reduction of the risks for the patient.

Furthermore, it is clear that modifications and variations may be made to the system described and illustrated herein.

For instance, each photodetector may be of a type different from what has been described. In general, it is possible to use any photodetector with a gain higher than unity, such as single SPADs, or else photodiodes operating in the linear regime in the proximity of the breakdown voltage.

In addition, the number of light sources in each lighting device, as well as the corresponding wavelengths of emission, may be different from what has been described previously and may vary according to the functional parameters that are to be determined. For instance, systems are possible in which each lighting device includes a single light source, which in turn may generate radiation at different wavelengths.

Furthermore, in general, the wavelengths of the light sources may be different from what has been described and may, for example, fall within portions of the spectrum other than the near infrared.

Further possible are systems that enable spectroscopic analyses different from continuous-wave spectroscopy to be carried out.

In addition, systems are possible in which the housings are coated with blackened paints, so as to prevent any undesired light absorption.

The shape of the wearable structure may change, for example according to the type of body tissue that is to be analyzed, since, as explained previously, the present fNIRS system is not limited to the analysis of just the brain tissue.

Figure 7:
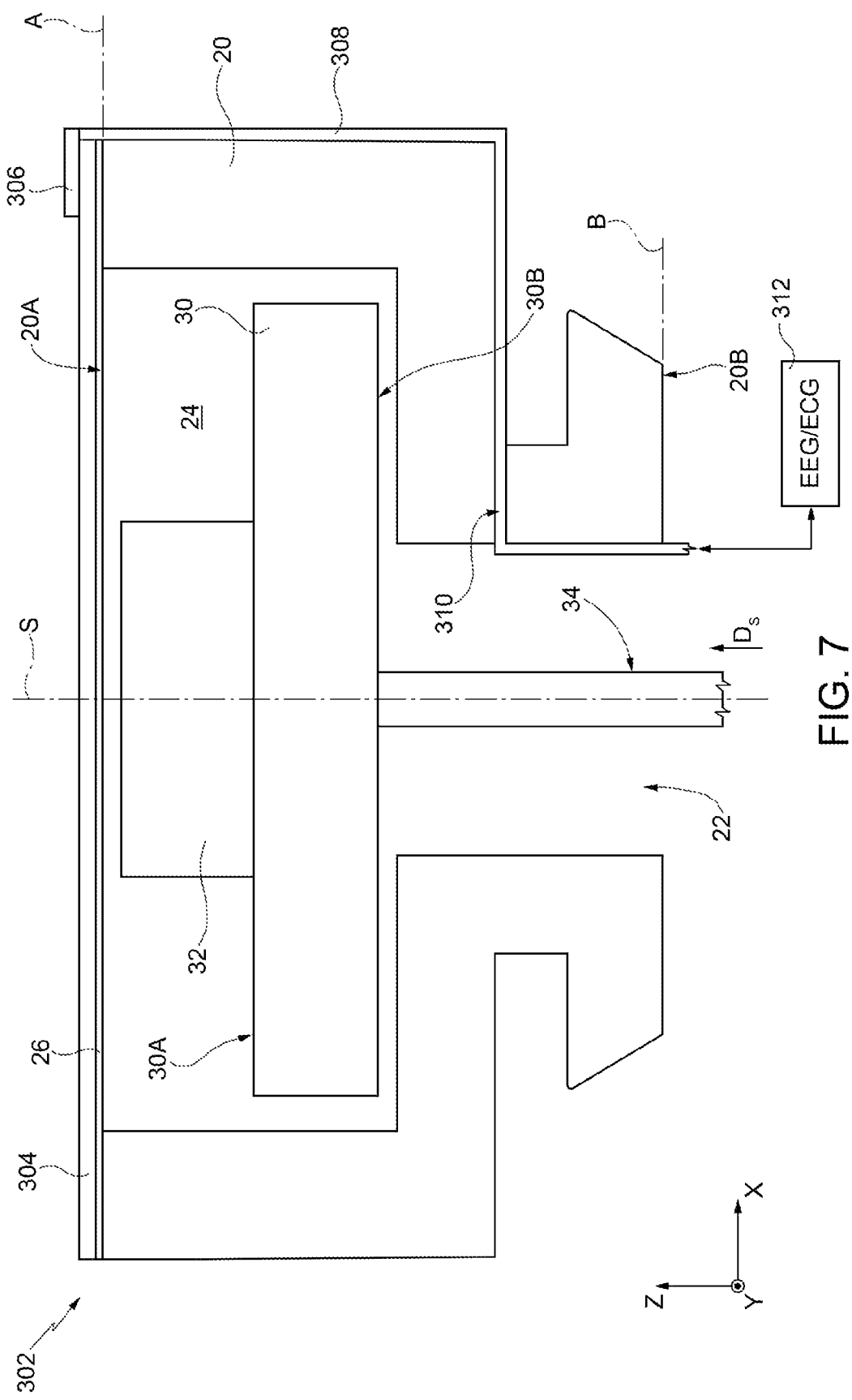
FIG. 7 is a schematic cross-sectional illustration of a variant of a lighting device.
Figure 8:
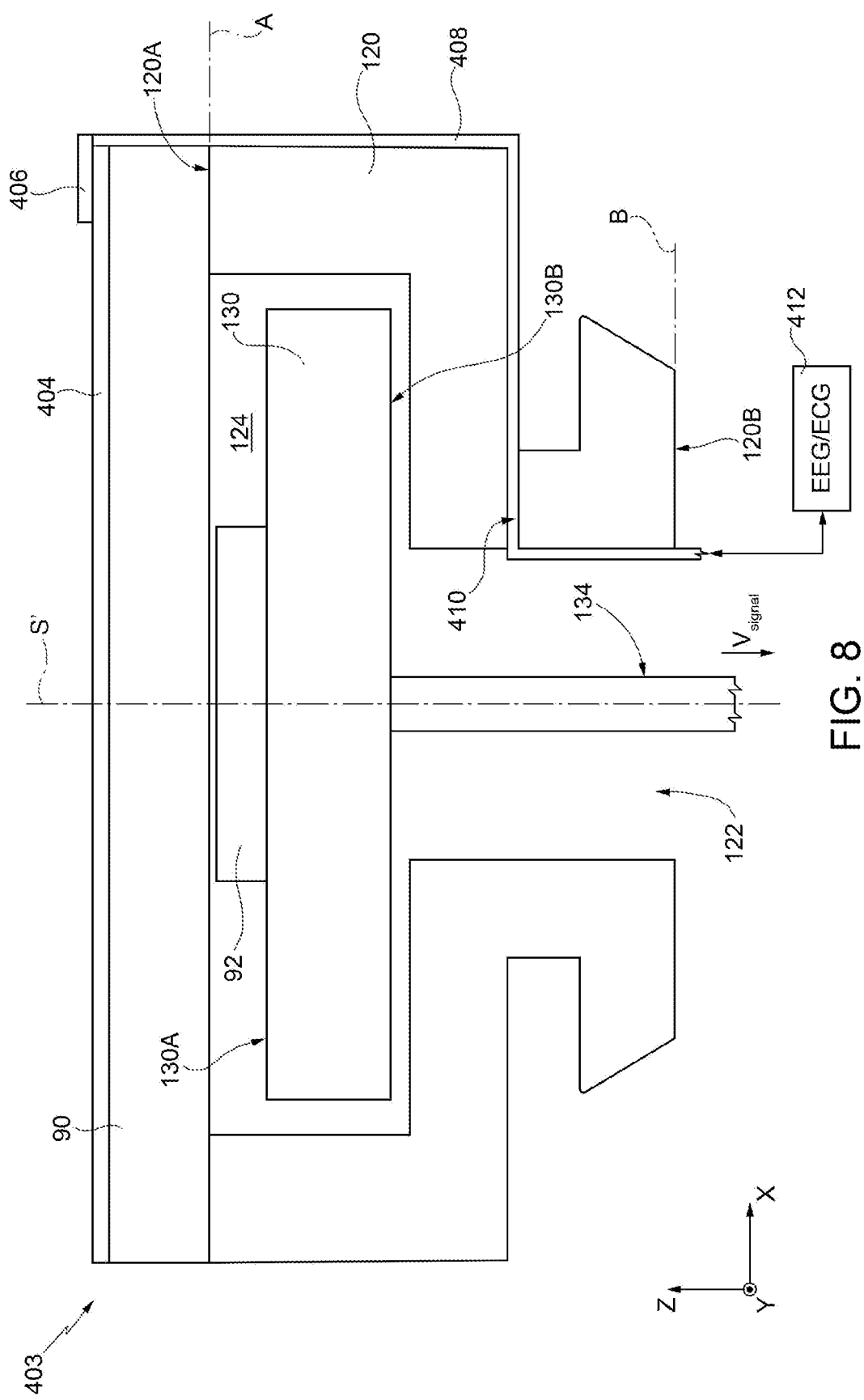
FIG. 8 is a schematic cross-sectional illustration of a variant of a detection device.

All this having been said, embodiments are possible, in which the lighting devices and/or the detection devices are of the type shown, respectively, in FIGS. 7 and 8.

In detail, as shown in FIG. 7, the lighting device (here designated by 302) further includes a top coating layer 304, arranged on top of the cap 26 and made up of a conductive material such as graphene or a conductive polymer (such as poly(3,4-ethyelenedioxythiophene):poly(styrene sulfonate), known as PEDOT-PSS) or a random network of nanowires (e.g., carbon nanotubes, silver nanowires). The top coating layer 304 is substantially transparent (i.e., with an optical transmittance greater than 85%) in the near infrared; therefore, the optical behavior of the lighting device 302 stays the same, irrespective of the presence of the top coating layer 304. In addition, the top coating layer 304 acts as an electrode, such as an electrode for electroencephalography (EEG) or electrocardiography (ECG) for the case of the PPG.

In greater detail, the top coating layer 304 includes a respective inner portion, which overlies, at a distance, the bicolor LED emitter 32, and a peripheral portion, which overlies a portion of the cap 26 in direct contact with the container 20; the top coating layer 304 is thus arranged in front of the bicolor LED emitter 32. The lighting device 302 may further include a contact region 306, arranged on the peripheral portion of the top coating layer 304 and made up of a layer of a metal such as gold, platinum or aluminum. In addition, the lighting device 302 may further include a conductive wire 308, made up of copper. The conductive wire 308 has a corresponding first end, which contacts the contact region 306. A first portion of the conductive wire 308 extends partially along the outer wall of the portion of the container 20 which delimits the main cavity 24; in addition, a second portion of the conductive wire 308 extends through a hole 310 through the container 20, this hole 310 giving out onto the secondary cavity 22; a third portion of the conductive wire 308 extends in the secondary cavity 22. The conductive wire 308 has a corresponding second end, which may be coupled, in use, to an EEG or ECG system 312. Although not shown, embodiments are possible in which the first portion of the conductive wire 308 extends in the main cavity 24.

As shown in FIG. 8, the detection device (here designated by 403) further includes a respective top coating layer 404, arranged on the optical filter 90 and made up of a conductive material such as graphene or a conductive polymer (such as PEDOT-PSS) or a random network of nanowires (e.g., carbon nanotubes, silver nanowires). The top coating layer 404 is substantially transparent (i.e., with an optical transmittance greater than 85%) in the near infrared; therefore, the optical behavior of the detection device 403 stays the same, irrespective of the presence of the top coating layer 404. In addition, the top coating layer 404 acts as an electrode, such as an EEG or ECG electrode in the case of the PPG.

In greater detail, the top coating layer 404 includes a respective inner portion, which overlies, at a distance, the photodetector 92, and a peripheral portion, which overlies a portion of the optical filter 90 in direct contact with the container 120; the top coating layer 404 is thus arranged in front of the photodetector 92. The detection device 403 may further include a respective contact region 406, arranged on the peripheral portion of the top coating layer 404 and made up of a layer of a metal such as gold, platinum or aluminum. In addition, the detection device 403 may further include a respective conductive wire 408, made up of, e.g., copper. The conductive wire 408 has a corresponding first end, which contacts the contact region 406. A first portion of the conductive wire 408 extends partially along the outer wall of the portion of the container 120 which delimits the main cavity 124; in addition, a second portion of the conductive wire 408 extends through a hole 410 through the container 120, this hole 410 giving out onto the secondary cavity 122; a third portion of the conductive wire 408 extends in the secondary cavity 122. The conductive wire 408 has a corresponding second end, which may be coupled, in use, to the EEG or ECG system, here designated by 412.

The top coating layers 304, 404 may also be disposable and applied on purpose onto the cap 26 and the optical filter 90.

Figure 9A:
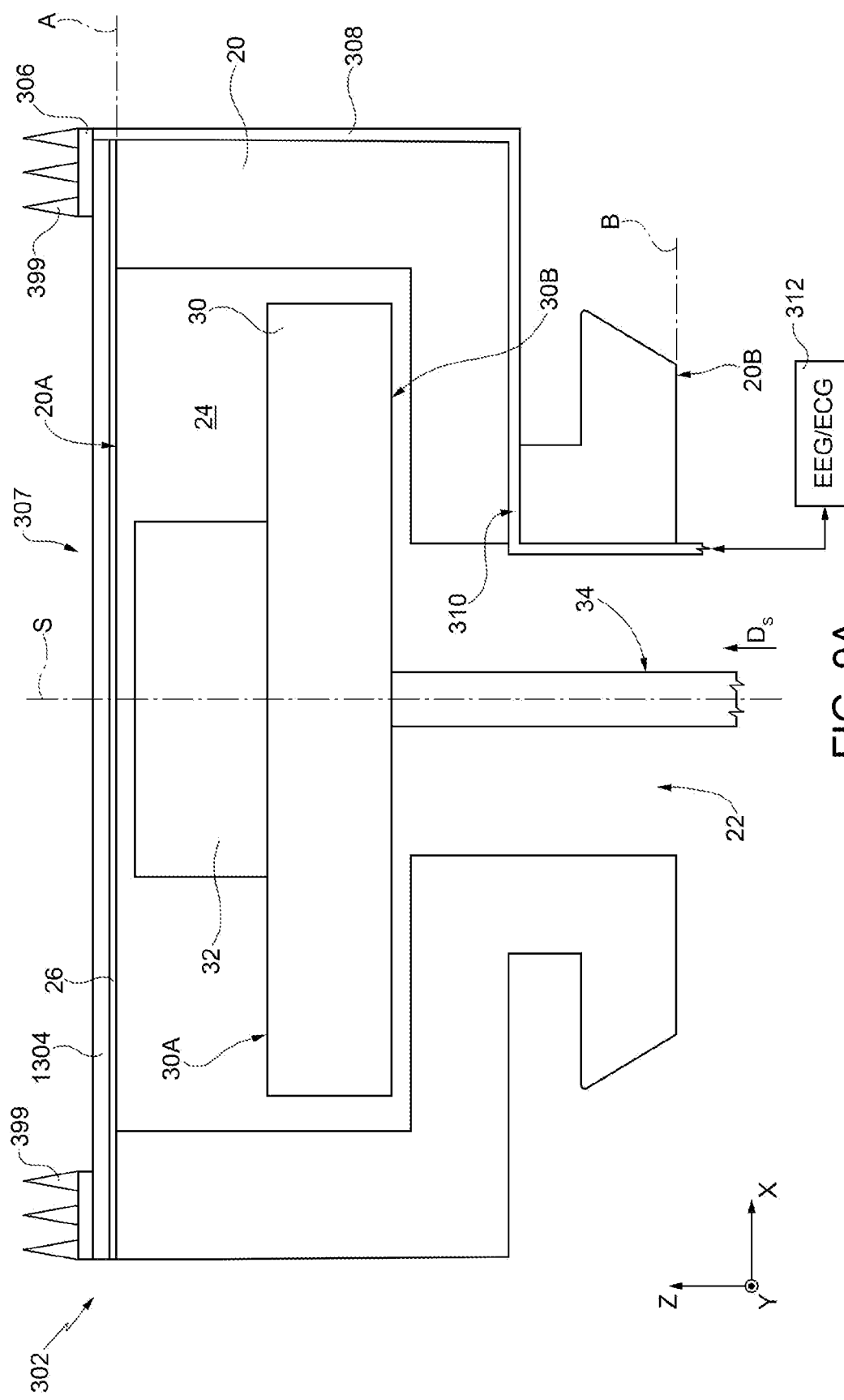
FIGS. 9A and 11A are schematic cross-sectional illustrations of variants of a lighting device.
Figure 9B:
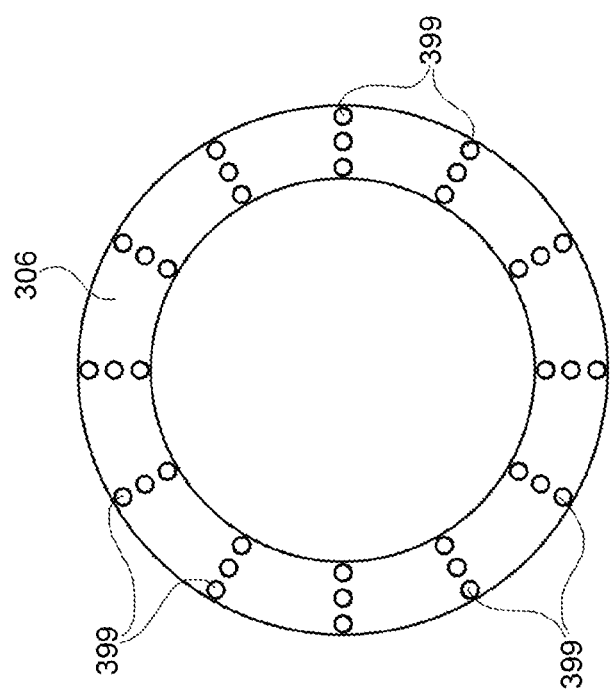

As shown in FIGS. 9A and 9B, a further embodiment is possible, which is described herein below with reference to the lighting device 302, though the same features may apply to the detection device 403.

In detail the contact region 306 has an annular shape, arranged on the peripheral portion of the top coating layer 304. Therefore, the contact region 306 laterally delimits an aperture 307, overlying, at a distance, the bicolor LED emitter 32.

In addition, the lighting device 302 includes a plurality of metallic needles 399, namely a plurality of metallic cones (namely, sharp elements), with bases arranged on the contact region 306 and axes parallel to the axis of symmetry S. The vertices of the cones are apt to contact the body of the patient, therefore the needles 399 and the contact region act as an electrode. The arrangement of the needles 399 shown in FIGS. 9a-9B is purely illustrative.

In the case of the embodiment shown in FIGS. 9A-9B, the top coating layer (here designated by 1304) may be made of a dielectric material, or it may even be absent, in which case (not shown), the contact region 306 is arranged on the cap 26. The top coating layer 1304 may also be of the same type as shown in FIG. 7.

Figure 10:
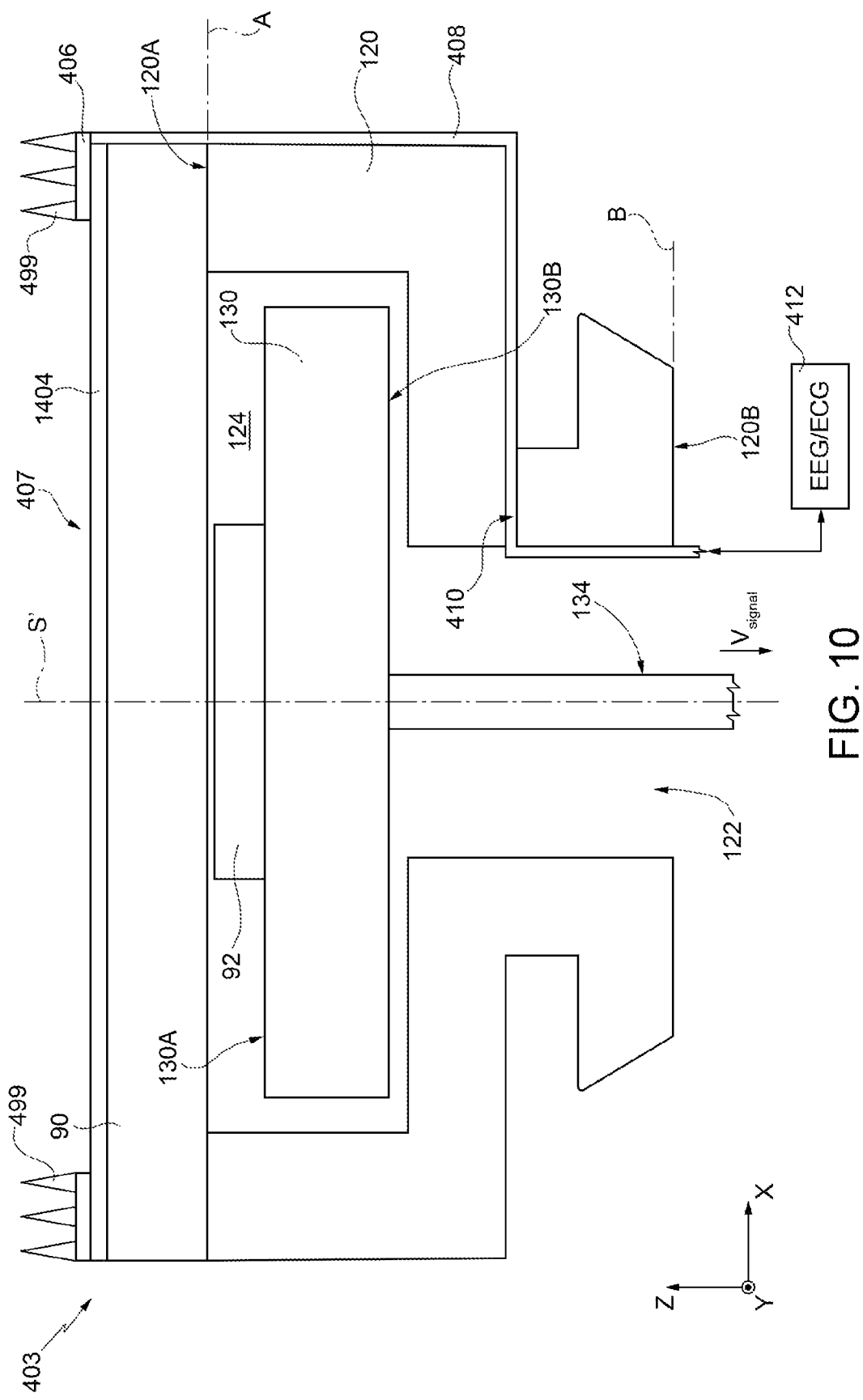
FIGS. 10 and 12 are schematic cross-sectional illustrations of variants of a detection device.

As mentioned before, the needles may be present also in the case of the detection device 403, as shown in FIG. 10. In particular, the needles, here designated by 499, are arranged on the contact region (here designated by 406), which has the same shape shown in FIGS. 9A-9B; the aperture, designated by 407, overlies the photodetector 92, at a distance. The top coating layer, designated by 1404, may be of dielectric material, or it may even be absent, in which case (not shown), the contact region 406 is arranged on the optical filter 90. The top coating layer 1404 may also be of the same type as shown in FIG. 8.

Figure 11B:
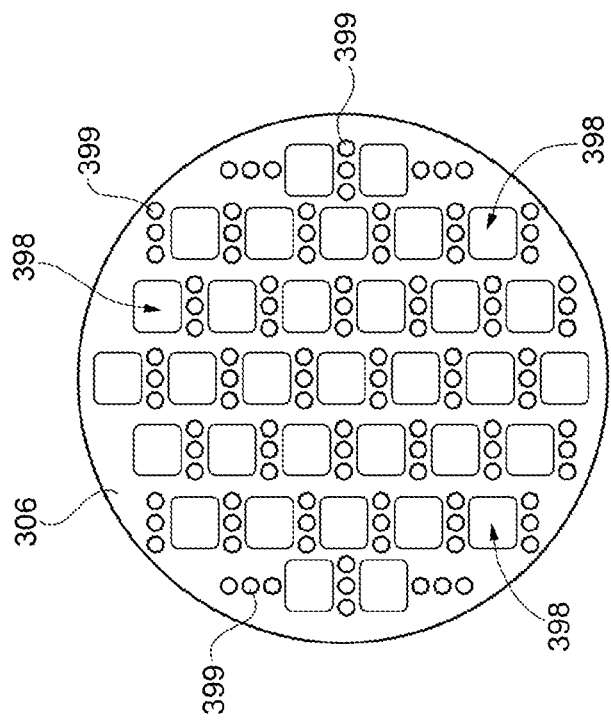
FIGS. 9B and 11B are schematic top plan views of portions of the lighting devices of, respectively, FIGS. 9A and 11A.
Figure 11A:
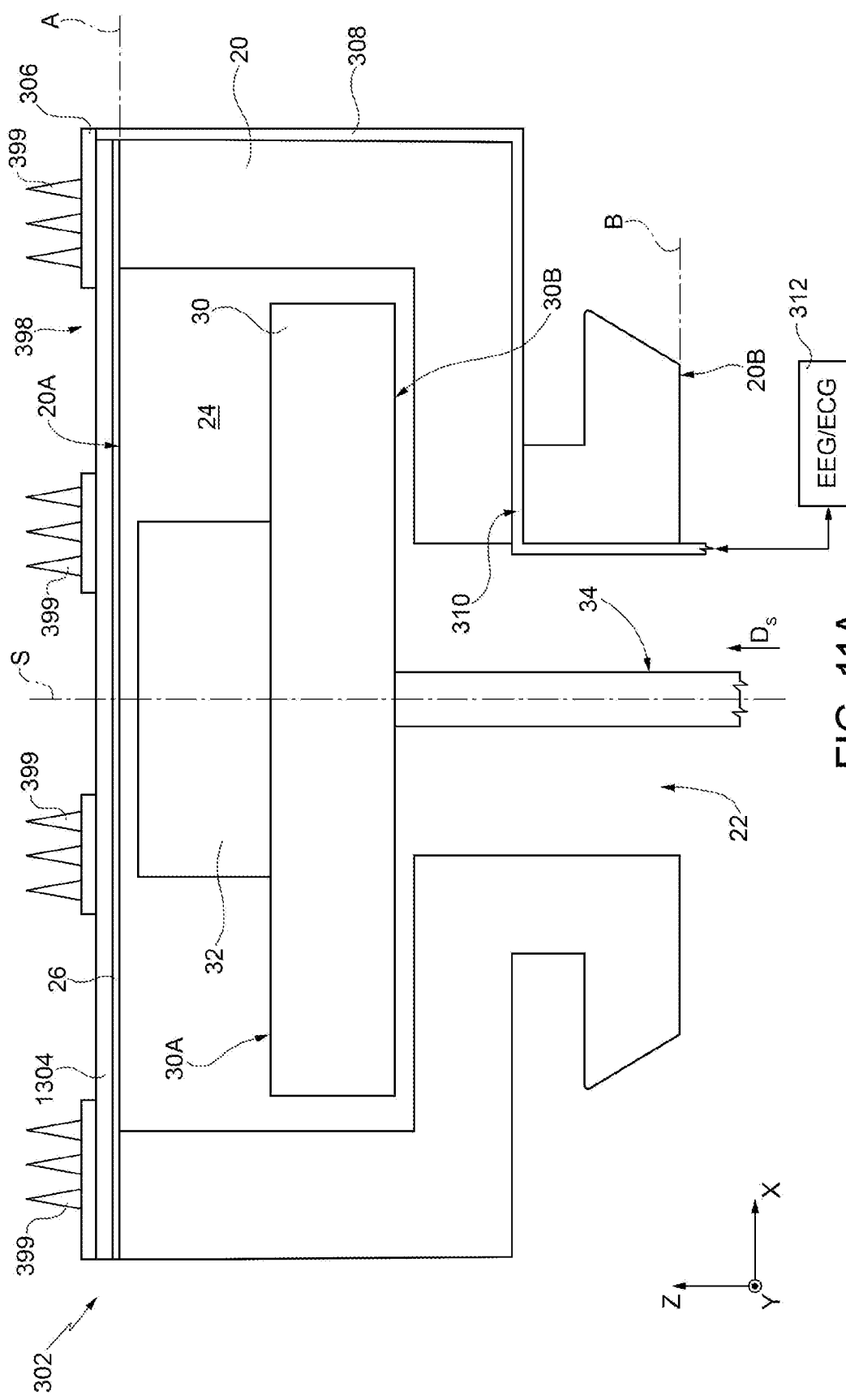

As shown in FIGS. 11A and 11B, a further embodiment is possible, which is described here below with reference to the lighting device 302, though the same features may apply also to the detection device 403.

In detail, the contact region 306 has the shape of a layer with a plurality of apertures 398, which give out onto corresponding portions of the top coating layer 1304, which may be made of a dielectric material; the top coating layer 1304 may even be absent, in which case (not shown), the contact region 306 is arranged on the cap 26 and the apertures 398 give out corresponding portions of the cap 26; at least one of the apertures 398 overlies the bicolor LED emitter 32. The needles 399 are arranged on the contact region 306, which has the same shape shown in FIGS. 9A-9B.

In case the top coating layer 1304 is of the same type as shown in FIG. 7 and the apertures 398 are uniformly distributed, the overall transmittance of the assembly formed by the top coating layer 1304 and the contact region 306 is given, to a first approximation, by product of i) the transmittance of the top coating layer 1304 and ii) the ratio between the overall area of the apertures 398 and the overall area of the coating layer 1304, in top plan view.

Figure 12:
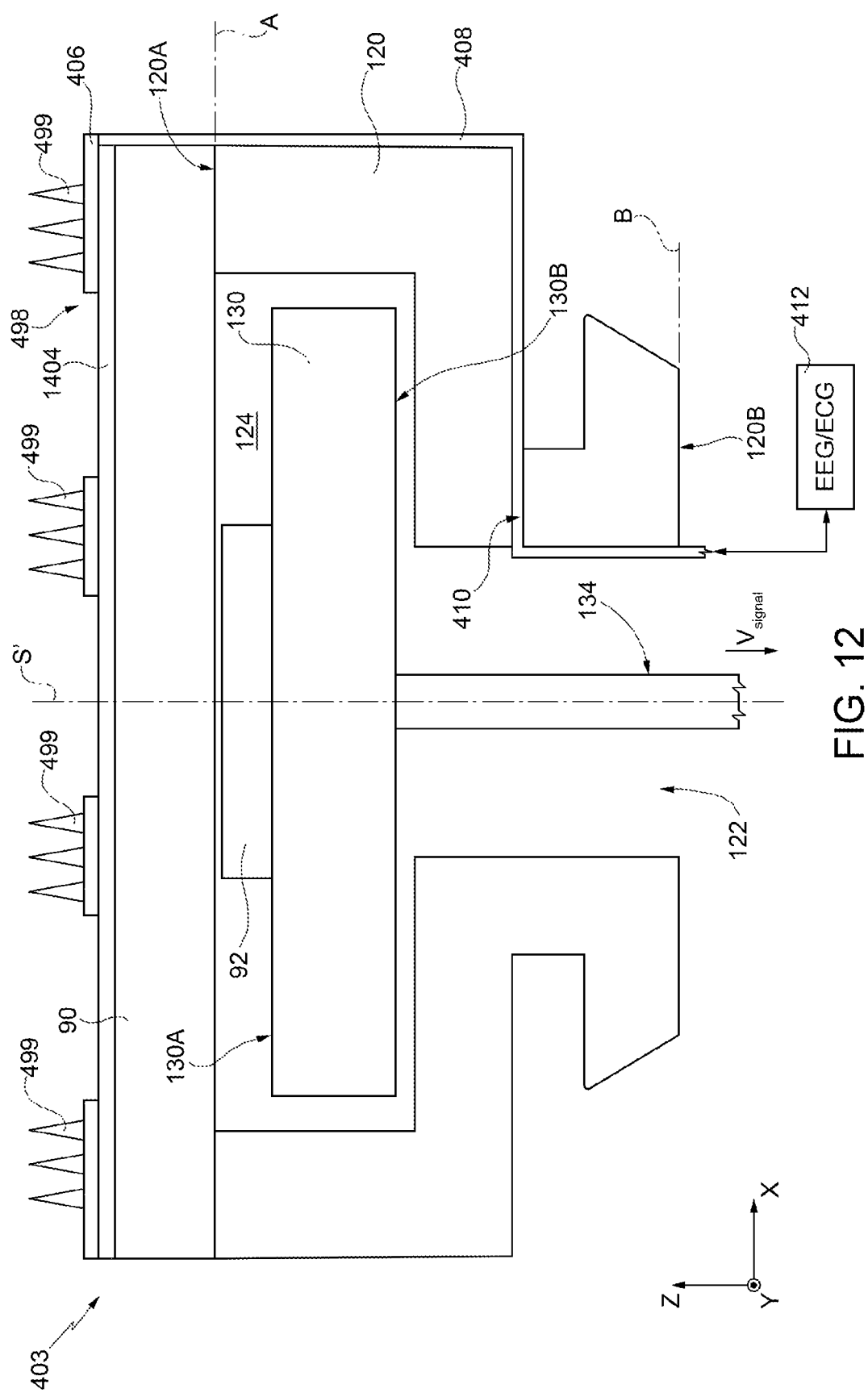

As shown in FIG. 12, a further embodiment is possible, in which the needles (designated by 499) are arranged on the contact region 406 of the detection device 403, which may have the same shape shown in FIGS. 11A-11B. In this case, the apertures 398 give out onto the top coating layer 1404, which may be made of a dielectric material. The top coating layer 1404 may even be absent, in which case (not shown), the contact region 406 is arranged on the optical filter 90. The top coating layer 1404 may also be of the same type as shown in FIG. 8.

Put in other words, the embodiments shown in FIGS. 7, 8, 9A-9B, 10, 11A-11B and 12 feature, each, a cover structure arranged on top of an active optical device. In particular, in the case shown in FIG. 7, the cover structure includes the cap 26 and the top coating layer 304; in the cases shown in FIGS. 9A-9B and 11A-11B, the cover structure includes the cap 26, the top coating layer 1304, the contact region 306 and the needles 399. In the case shown in FIG. 8, the cover structure includes the optical filter 90 and the top coating layer 404; in the cases shown in FIGS. 10 and 12, the cover structure includes the optical filter 90, the contact region 406 and the needles 499. In the case of the lighting devices 302, the cover structure is crossed by the light generated by the bicolor LED emitter 32; in the case of the detection devices 403, the cover structure is crossed by the light to be detected by the photodetector 92.

Although not shown, further embodiments are possible, in which the needles have rounded vertices, i.e., rounded end portions apt to contact the body.

Finally, it has to be noted that the present system may form a photopletysmography (PPG) system, rather than a fNIRS system.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
   an optical device including:
      a housing including an external surface and an external sidewall transverse to the external surface; and
      at least one of a photodetector or a first light source;
   a cap on the external surface of the housing of the optical device;
   an electrode on the cap, the electrode being configured to contact, in use, a body tissue; and
   a conductive wire coupled to the electrode, the conductive wire extends along the external sidewall of the housing.

2. The device according to claim 1, wherein the electrode includes a conductive layer which overlies the optical device and has a transmittance greater than 85% for wavelengths between 650 nm and 950 nm.

3. The device according to claim 2, wherein the conductive layer includes at least one of graphene, a conductive polymer, or a random network of nanowires.

4. The device according to claim 3, wherein the electrode further comprises:
   a metallic planar region, arranged on the conductive layer and laterally delimiting at least one aperture overlying the optical device; and
   a plurality of elongated metallic elements extending from the metallic planar region and configured to contact, in use, the body tissue.

5. The device according to claim 1, wherein the cap further includes a dielectric layer overlying the optical device, and the electrode further includes:
   a metallic planar region, arranged on the dielectric layer and laterally delimiting at least one aperture overlying the optical device; and
   a plurality of elongated metallic elements extending from the metallic planar region and configured to contact, in use, the body tissue.

6. The device of claim 1, wherein the housing further includes:
   a first side and a second side opposite to the first side;
   a first cavity closer to the first side than the second side; and
   a second cavity closer to the second side than the first side.

7. The device of claim 6, wherein:
   the first cavity is cylindrical and has a first diameter;
   the second cavity is cylindrical and has a second diameter less than the first diameter.

8. The device of claim 6, wherein the conductive wire extends through the housing to the second cavity of the housing.

9. The device of claim 1, wherein the cap includes an optical filter.

10. A device, comprising:
    a housing which defines a first cavity and a second cavity;
    a substrate in the first cavity;
    an optical structure on the substrate, the optical structure including at least one of a photodetector or a light source;
    a dielectric cap on the first cavity, the first cavity disposed between the dielectric cap and the second cavity; and
    an electrode on the dielectric cap, the electrode being configured to contact, in use, a body tissue, the electrode includes:

a metallic planar region on the dielectric cap and laterally delimiting at least one aperture overlying the optical structure; and a plurality of elongated metallic elements extending from the metallic planar region and configured to contact, in use, the body tissue.

11. The device of claim 10, wherein the electrode includes a conductive layer which overlies the optical device and has a transmittance greater than 85% for wavelengths between 650 nm and 950 nm.

12. The device of claim 10, further comprising an electrical cable electrically coupled to the optical structure and extending from the first cavity through the second cavity.

13. The device of claim 10, wherein:
the first cavity is cylindrical and has a first diameter; and
the second cavity is cylindrical and has a second diameter less than the first diameter.

14. A device, comprising:
a housing having a first side opposite to a second side:
a first cavity closer to the first side than the second side, the first cavity is cylindrical and has a first diameter; and
a second cavity closer to the second side than the first side, the second cavity is cylindrical and has a second diameter that is less than the first diameter;
a substrate in the first cavity;
an optical emitter on the substrate and closer to the first side than the substrate;
a cap on the first side of the housing, the cap being on the first cavity; and
an electrode on the cap on the first side of the housing.

15. The device of claim 14, further comprising a cable coupled to the substrate and extending through the second cavity.

16. The device of claim 15, wherein the cable extends from an external surface or sidewall of the housing to the second cavity of the housing.

17. The device of claim 14, comprising a conductive layer on the cap.

18. The device of claim 17 wherein the conductive layer is graphene.

19. The device of claim 17, comprising an electrical connection and a hole between inner walls of the housing, the electrical connection through the hole.

20. The device of claim 19 wherein the electrical connection extends into the second cavity through the hole.

* * * * *